US008868393B2

(12) United States Patent
Liu

(10) Patent No.: US 8,868,393 B2
(45) Date of Patent: Oct. 21, 2014

(54) ALGORITHMS FOR CLASSIFICATION OF DISEASE SUBTYPES AND FOR PROGNOSIS WITH GENE EXPRESSION PROFILING

(71) Applicant: Roche Molecular System, Inc., Pleasanton, CA (US)

(72) Inventor: Wei-Min Liu, Dublin, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 13/889,262

(22) Filed: May 7, 2013

(65) Prior Publication Data

US 2013/0245962 A1    Sep. 19, 2013

Related U.S. Application Data

(62) Division of application No. 12/578,417, filed on Oct. 13, 2009, now Pat. No. 8,463,590.

(60) Provisional application No. 61/104,998, filed on Oct. 13, 2008.

(51) Int. Cl.
*G06G 7/48* (2006.01)
*G06F 19/20* (2011.01)
*G06F 19/24* (2011.01)

(52) U.S. Cl.
CPC ............... *G06F 19/20* (2013.01); *G06F 19/24* (2013.01)
USPC .......................................................... 703/11

(58) Field of Classification Search
USPC .......................................................... 703/11
See application file for complete search history.

(56) References Cited

U.S. PATENT DOCUMENTS

2006/0063156 A1*   3/2006   Willman et al. .................. 435/6
2006/0147926 A1    7/2006   Emmert-Buck et al.
2010/0028876 A1*   2/2010   Gordon et al. .................... 435/6

OTHER PUBLICATIONS

Wang et al., "Characterization of mismatch and high-signal intensity probes associated with Affymetrix genechips", Bioinformatics, 2007, vol. 23, No. 16, pp. 2088-2095.
Bolstad et al., "Quality Assessment of Affymetrix GeneChip Data," Statistics for Biology and Health (2005) Part I, pp. 33-47.
Brown et al., "Interval Estimation for a Binomial Proportion", 2001, Statistical Sciences, V. 16, pp. 101-133.
Chang et al., "LIBSVM—A Library for Support Vector Machines", located at http://www.csie.ntu.edu.tw/.about.cjlin/libsvm/ last accessed on May 5, 2010, 4 pages.
Cortes et al., "Support-Vector Networks", Machine Learning, 1995, v. 20, pp. 273-297.
Fodor et al., "Light directed, Spatially Addressable Parallel Chemical Synthesis", Science, 1991, V. 251, pp. 767-773.
Greenberg et al., "International Scoring System for Evaluating Prognosis in Myelodysplastic Syndromes", 1997, Blood, v. 89, pp. 2079-2088.
Hosmer et al., Applied Survival Analysis: Regression Modeling of Time to Event Data, 1999, Wiley, New York., table of contents, 5 pages.
Hougaard et al., "Analysis of Multivariate Survival Data", 2002, Springer-Verlag, New York., table of contents, 12 pages.
Liu et al., "Analysis of high-density expression microarrays with signed-rank call algorithms", Bioinformatics, 2002, V. 18, No. 12, pp. 1593-1599.
Liu et al., "Assessment of Impact of Protocol changes on Classification Accuracy", 2007, Proceedings of the Joint Statistical Meetings, American Statistical Association, Alexandria, VA, pp. 2458-2459.
Liu et al.,"PQN and DQN: Algorithms for Expression Microarrays," J. Theoretical Biol., 2006, V. 243, p. 273-278.
Meyer et al., "Support vector machines: The interface to libsvm in package e1071", 2006, Technishe Universitat Wien, Austria, 8 pages.
Paik et al., "A Multigene Assay to predict recurrence of tamoxifen-treated, node-negative breast cancer", 2004, N. Engl. J. Med., V. 351, pp. 2817-2826.
Scholkoph et al., "Learning with Kernels: Support Vector Machines, Regularization, Optimization and Beyond", 2002, MIT Press, Cambridge, MA., table of contents, 7 pages.
Simon et al., "Design and Analysis of DNA Microarray Investigations", 2003, Springer, New York., table of contents, 6 pages.
Vapnik et al., The Nature of Statistical Learning Theory (2.sup.nd), Library of Congress Cataloging-in-Publication Data, 1999, Springer, NY., table of contents, 9 pages.

* cited by examiner

*Primary Examiner* — Jerry Lin
(74) *Attorney, Agent, or Firm* — Kilpatrick Townsend & Stockton LLP

(57) ABSTRACT

Methods for generating a normalized expression signal for microarray data based on a theoretical distribution at the unit level to produce a normalized expression signal for the single microarray that is independent of other microarrays. The method typically includes receiving microarray data representing a plurality of probe pairs for a single microarray, determining, for each probe pair, differences between intensities of perfect match (PM) probes and intensities of mismatched (MM) probes, determining a difference signal, D, based on the determined differences, and scaling the difference signal, D, to produce an expression signal, DS. The method also typically includes normalizing the expression signal based on a theoretical distribution at the unit level to produce a normalized expression signal for the single microarray that is independent of other microarrays.

20 Claims, 7 Drawing Sheets

Summary of Expression Signals

FIG. 4 Summary of Quality Measures

Class Pair (Dn3_1922 Set 5)
r=M623(14) g=B082(14) b=L050(14) br=G050(14)

Projection plot of four testing data in class 14 with training data

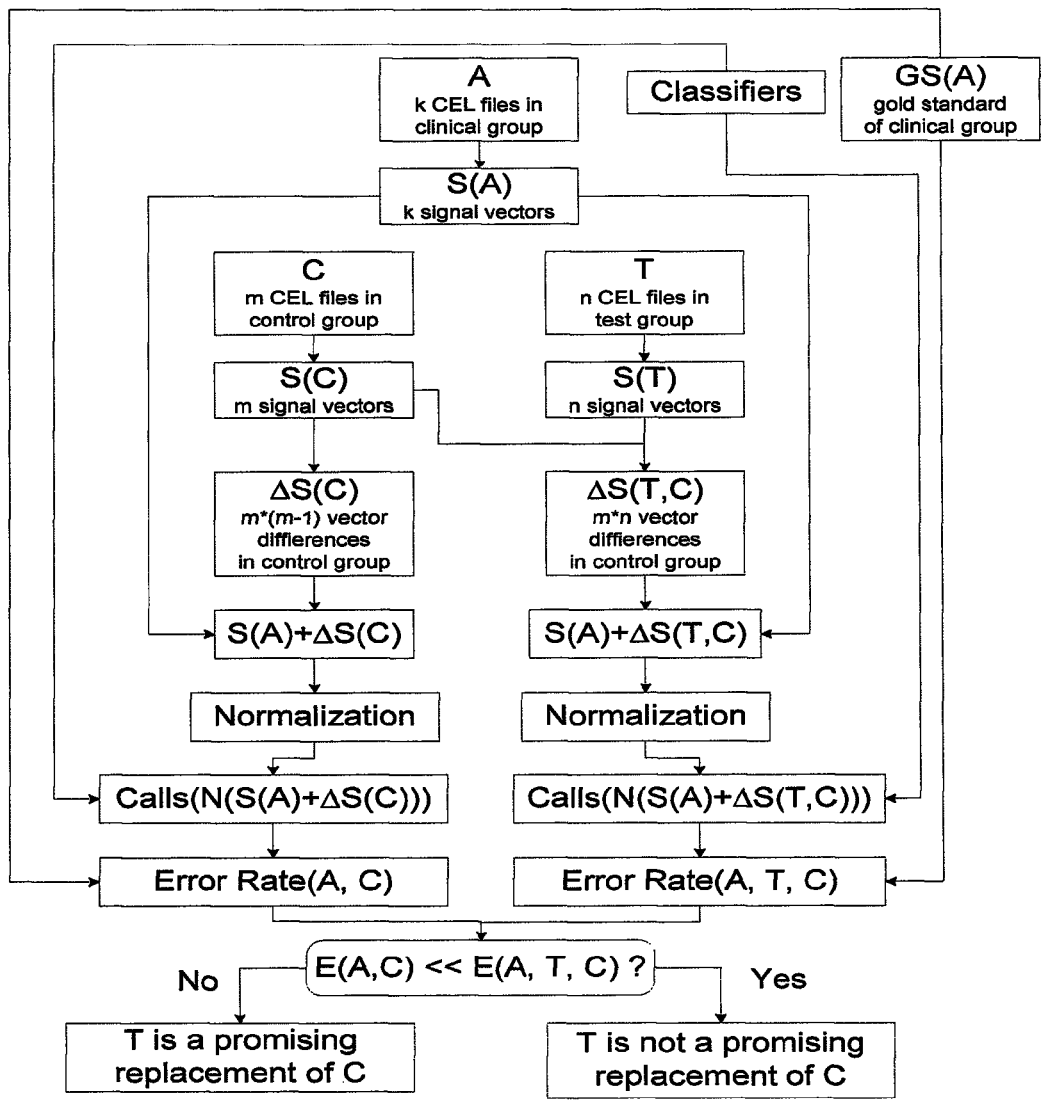
FIG. 8: Flow chart of the IASCCA algorithm.

ALGORITHMS FOR CLASSIFICATION OF DISEASE SUBTYPES AND FOR PROGNOSIS WITH GENE EXPRESSION PROFILING

CROSS-REFERENCES TO RELATED APPLICATIONS

This application is a divisional of U.S. patent application Ser. No. 12/578,417, filed Oct. 13, 2009 which claims the benefit of U.S. Provisional Application Ser. No. 61/104,998, filed Oct. 13, 2008, the disclosures of which are incorporated herein by reference in its entirety.

BACKGROUND

The present invention relates generally to analysis of data generated by expression arrays, and more particularly to classification of leukemia based on expression profiles obtained from expression arrays.

Bioinformatics plays an important role in biomedical research. For example, analysis of data from oligonucleotide microarrays can lead to the detection of differential RNA expression and genotypes or mutations in DNA. An expression profile that indicates what genes are expressed during certain disease conditions provides a signature for diseases. For diseases such as Leukemia it is desirable to determine the causes and categorize the type of Leukemia from which a patient may be suffering. There are generally many causes of Leukemia, and it is desirable to accurately classify the type of Leukemia and provide an accurate diagnosis so that the appropriate treatment may be applied. One current method for classifying Leukemia involves a cytologist visually inspecting a patient sample subjected to biological analysis. Such a method is time consuming and may produce different results if examined by different specialists. Additionally, because different types of Leukemia respond to different treatments, if the wrong classification is made, an ineffective treatment may be applied, thereby wasting time that could otherwise be used for applying a more effective treatment.

Therefore it is desirable to provide systems and methods that overcome the above and other problems. In particular, it is desirable to provide systems and methods that automatically and accurately classify diseases based on expression profile data.

BRIEF SUMMARY

The present invention provides systems and methods for analyzing data generated by expression arrays. In various embodiments, systems and methods are provided for classifying diseases such as leukemia based on expression profiles obtained from expression arrays.

According to one embodiment, one or more processing modules are provided for the generation of expression signals, analysis of data quality, determination of classification calls and the support of other analysis tools.

According to one aspect of the present invention, a method is provided for generating an expression signal based on microarray data. The method typically includes receiving microarray data representing a plurality of probe pairs for a single microarray, determining, for each probe pair, differences between intensities of perfect match (PM) probes and intensities of mismatched (MM) probes, determining a difference signal, D, based on the determined differences, and scaling the difference signal, D, to produce an expression signal, DS. The method also typically includes normalizing the expression signal based on a theoretical distribution at the unit level to produce a normalized expression signal for the single microarray that is independent of other microarrays.

According to another aspect of the present invention, a method is provided for invalidating a microarray experiment using a quality control measure. The method typically includes receiving microarray data representing a plurality of probes on a microarray, generating an expression signal based on the microarray data, automatically determining a quality control measure, and automatically invalidating the entire array experiment in response to the quality control measure. In certain aspects, the quality control measure is a percentage of present calls measure.

According to yet another aspect of the present invention, a method is provided for automatically classifying microarray data. The method typically includes receiving microarray data representing a plurality of probes on a microarray, automatically generating an expression signal based on the microarray data, applying a first classification model for a classification scheme having a plurality of classes to a portion of the microarray data to produce a first preliminary call, and applying a second classification model for the classification scheme to the portion of the microarray data to produce a second preliminary call. The method also typically includes combining the first and second preliminary calls to produce a combined call and a weight, determining whether the weight exceeds a threshold value, and if not, returning an Indeterminable Call, and if so, comparing the combined call with a verifier to determine consistency, and if the combined call is not consistent with the verifier, returning an Indeterminable Call, and if the combined call is consistent with the verifier, returning combined call, the combined call identifying a class in the classification scheme. In certain aspects, each of the first and second classification models includes a set of linear classifiers for class pairs. In certain aspects, the verifier includes the output of a classification model that includes a set of linear classifiers for all classes. In certain aspects, the classification schema is a 19 class schema, and wherein the method further includes comparing the combined call with a second verifier to determine consistency.

According to a further aspect, a tangible computer readable medium that stores code, which when executed by one or more processors cause the processor(s) to automatically classify microarray data. The code typically includes instructions to automatically generate an expression signal based on microarray data representing a plurality of probes on a microarray, to apply a first classification model for a classification scheme having a plurality of classes to a portion of the microarray data to produce a first preliminary call, to apply a second classification model for the classification scheme to the portion of the microarray data to produce a second preliminary call, and to combine the first and second preliminary calls to produce a combined call and a weight. The code also typically includes instructions to determine whether the weight exceeds a threshold value, and if not, to return an Indeterminable Call, and if so, to compare the combined call with a verifier to determine consistency, and if the combined call is not consistent with the verifier, to return an Indeterminable Call, and if the combined call is consistent with the verifier, to return a combined call, the combined call identifying a class in the classification scheme.

According to yet a further aspect, a tangible computer readable medium that stores code, which when executed by one or more processors cause the processor(s) to automatically invalidate a microarray experiment using a quality control measure. The code typically includes instructions to generate an expression signal based on microarray data representing a plurality of probes on a microarray, to automatically determine a quality control measure, and to automatically invalidate the entire array experiment in response to the quality control measure.

According to still a further aspect, a tangible computer readable medium that stores code, which when executed by one or more processors cause the processor(s) to generate a normalized expression signal, based on microarray data. The code typically includes instructions to receive microarray data representing a plurality of probe pairs for a single microarray, to determine, for each probe pair, differences between intensities of perfect match (PM) probes and intensities of mismatched (MM) probes, to determine a difference signal, D, based on the determined differences, and to scale the difference signal, D, to produce an expression signal. The code also typically includes instructions to normalize the expression signal based on a theoretical distribution at the unit level to produce a normalized expression signal for the single microarray that is independent of other microarrays.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 8 is flow chart of an Impact of Additive Signal Changes on Call Accuracy (IASCCA) process according to one embodiment.

DETAILED DESCRIPTION

General Overview

Figure 1:
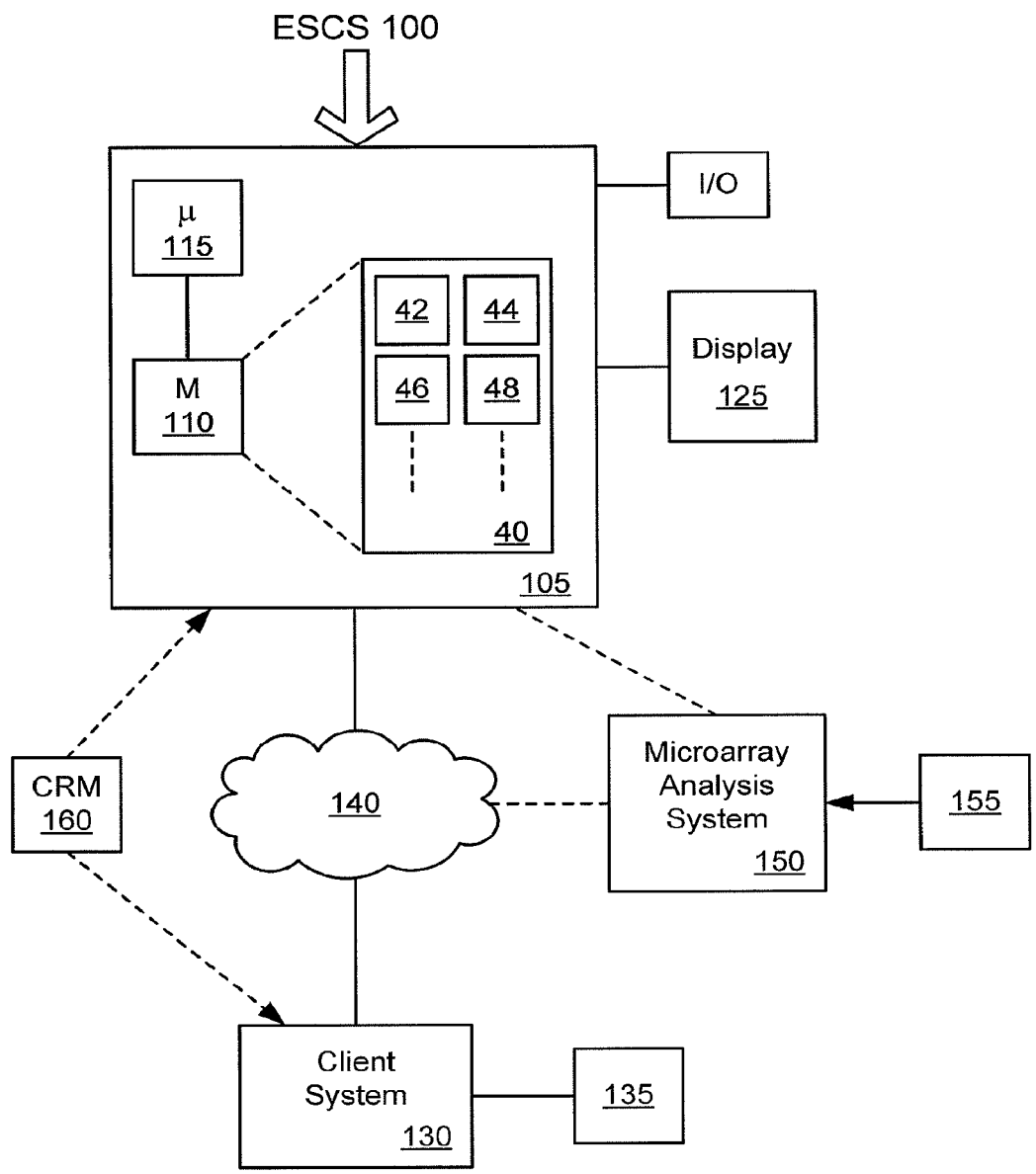
FIG. 1 illustrates an expression signal classification system (ESCS) 100 where aspects and embodiments of the present invention might be implemented.

The present invention provides systems and methods for classifying target molecules based on expression profiles obtained from expression arrays. In certain embodiments, the systems and methods are particularly useful for classifying Leukemia and other diseases.

"A target molecule" refers to a biological molecule of interest. The biological molecule of interest can be a ligand, receptor, peptide, nucleic acid (oligonucleotide or polynucleotide of RNA or DNA), or any other biological molecule. For example, if transcripts of genes are the interest of an experiment, the target molecules would be the transcripts. Other examples include protein fragments, small molecules, etc. "Target nucleic acid" refers to a nucleic acid (often derived from a biological sample) of interest. Frequently, a target molecule is detected using one or more probes. As used herein, a "probe" is a molecule for detecting a target molecule. It can be any of the molecules in the same classes as the target referenced above. A probe may refer a nucleic acid, such as an oligonucleotide, capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases. In addition, the bases in probes may be joined by a linkage other than a phosphodiester bond, so long as the bond does not interfere with hybridization. Thus, probes may be peptide nucleic acids in which the constituent bases are joined by peptide bonds rather than phosphodiester linkages. Other examples of probes include antibodies used to detect peptides or other molecules, any ligands for detecting its binding partners. When referring to targets or probes as nucleic acids, it should be understood that these are illustrative embodiments only.

In certain embodiments, probes may be immobilized on substrates to create an array. An "array" may comprise a solid support with peptide or nucleic acid or other molecular probes attached to the support. Arrays typically comprise a plurality of different nucleic acids or peptide probes that are coupled to a surface of a substrate in different, known locations or to a plurality of surface elements or features such as micro-beads. These arrays, also described as "microarrays" or colloquially "chips" have been generally described in the art, for example, in Fodor et al., Science, 251:767-777 (1991), which is incorporated by reference for all purposes. Methods of forming high density arrays of oligonucleotides, peptides and other polymer sequences with a minimal number of synthetic steps are well known in the art and need not be described here. Methods for making and using molecular probe arrays, particularly nucleic acid probe arrays are also well known.

Typically, a nucleic acid sample is a labeled with a signal moiety, such as a fluorescent label. The sample is hybridized with the array under appropriate conditions. The arrays are washed or otherwise processed to remove non-hybridized sample nucleic acids. The hybridization is then evaluated by detecting the distribution of the label on the chip. The distribution of label may be detected by scanning the arrays to determine florescence intensities distribution. Typically, the hybridization of each probe is reflected by several pixel intensities. The raw intensity data may be stored in a data file, such as a gray scale pixel intensity file.

According to one embodiment, an expression signal classification system (ESCS) includes one or more processing module(s) adapted to generate expression signals for expression arrays, to analyze data quality, to determine classification calls and to support other analysis tools. It should be appreciated that the various embodiments herein, while discussed with respect to expression microarrays, are also applicable to genotyping microarrays and other microarrays or related systems such as micro-bead systems. Additionally, specific examples are given with respect to classifying Leukemia, however, it should be understood that the systems and methods disclosed herein are useful for classifying other diseases such as Lymphoma or other diseases of interest.

Appendix A includes various definitions and abbreviations for terminology used herein.

System Overview

FIG. 1 illustrates an expression signal classification system (ESCS) 100 where aspects and embodiments of the present invention might be implemented. As shown, ESCS 100 includes ESCS computer system 105 having one or more processors 115 and memory module 110 as shown. Computer system 105 also includes communication modules (not shown) for transmitting and receiving information over one or more direct connections (e.g., USB, Firewire or other interface) and one or more network connections (e.g., including a modem or other network interface device). Memory module 110 may include internal memory devices and one or more external memory devices. Computer 105 also includes a display module 125, such as a monitor or printer. In one aspect, computer 105 receives data such as patient test results from microarray analysis system 150, or other test result source, either through a direct connection or over a network 140. For example, analysis system 150 may be configured to run microarray tests on one or more samples 155 and automatically provide the microarray test results data to computer 105. Typically, the microarray data will include pixel intensity data. Test system 150 may be directly coupled to computer system 105, or it may be remotely coupled over network 140. Computer 105 may also communicate data to and from one or more client systems 130 over network 140 as is well known. For example, a requesting physician may obtain and view a report from ESCS computer 105, which may be resident in a laboratory or hospital, using a client system 130.

Network 140 can be a LAN (local area network), WAN (wide area network), wireless network, point-to-point network, star network, token ring network, hub network, or other configuration. As the most common type of network in current use is a TCP/IP (Transfer Control Protocol and Internet Protocol) network such as the global internetwork of networks often referred to as the "Internet" with a capital "I," that will be used in many of the examples herein, but it should be understood that the networks that the present invention might use are not so limited, although TCP/IP is the currently preferred protocol.

Several elements in the system shown in FIG. 1 may include conventional, well-known elements that need not be explained in detail here. For example, computer 105 could include a desktop personal computer, workstation, mainframe, laptop, etc. Each client system 130 could include a desktop personal computer, workstation, laptop, PDA, cell phone, or any WAP-enabled device or any other computing device capable of interfacing directly or indirectly to the Internet or other network connection. Computer 105 could be resident in a specialized system, e.g., combined with microarray analysis system 150.

Client system 130 typically runs an HTTP client, e.g., a browsing program, such as Microsoft's Internet Explorer™ browser, Netscape's Navigator™ browser, Opera's browser, or a WAP-enabled browser in the case of a cell phone, PDA or other wireless device, or the like, allowing a user of client system 130 to access, process and view information and pages available to it from computer 105 over network 140. Each client system 130 also typically includes one or more user interface devices, such as a keyboard, a mouse, touch screen, pen or the like, for interacting with a graphical user interface (GUI) provided by the browser on a display (e.g., monitor screen, LCD display, etc.) 135 in conjunction with pages, forms and other information provided by computer 105. As discussed above, the present invention is suitable for use with the Internet, which refers to a specific global internetwork of networks. However, it should be understood that other networks can be used instead of the Internet, such as an intranet, an extranet, a virtual private network (VPN), a non-TCP/IP based network, any LAN or WAN or the like.

According to one embodiment, each client system 130 and all of its components are operator configurable using applications, such as a browser, including computer code run using a central processing unit such as an Intel Pentium processor or the like. Similarly, ESCS computer 105 and all of its components might be operator configurable using application(s) including computer code run using a central processing unit 115 such as an Intel Pentium processor or the like, or multiple processing units. Computer code for operating and configuring ESCS computer 105 to process microarray test results data as described herein is preferably downloaded and stored on a hard disk, but the entire program code, or portions thereof, may also be stored in any other tangible computer readable medium (e.g., volatile or non-volatile memory medium or device as is well known, such as a ROM or RAM) or provided on any portable, tangible computer readable medium 160 capable of storing program code, such as a compact disk (CD) medium, digital versatile disk (DVD) medium, a floppy disk, and the like. Additionally, the entire program code, or portions thereof, may be transmitted and downloaded from a software source, e.g., over the Internet, or from a server, as is well known, or transmitted over any other conventional network connection as is well known (e.g., extranet, VPN, LAN, etc.) using any communication medium and protocols (e.g., TCP/IP, HTTP, HTTPS, Ethernet, etc.) as are well known. It will also be appreciated that computer code for implementing aspects of the present invention can be implemented in any programming language that can be executed on a computer system such as, for example, in C, C+, HTML, Java, JavaScript, or any other scripting language, such as VBScript, or any other language.

According to one embodiment, an application module 40 includes instructions for implementing the various data processing processes discussed herein, as well as providing user interface configuration capabilities. Application 40 is preferably downloaded and stored in memory 110 (or other memory such as a local or attached RAM or ROM), although application module 40 can be provided on any software storage medium such as a floppy disk, CD, DVD, etc. as discussed above. In one embodiment, application module 40 includes various software modules for processing data content. For example, a communication interface module may be provided for communicating text and data to a display driver for rendering images (e.g., GUI images) on display 125, and for communicating with various I/O devices and/or another computer or server system in network embodiments. A user interface module may be provided for receiving user input signals from a coupled or remote user input device.

Expression Signal Generation, Classification and Quality Control

According to one embodiment, application module 40 also includes an expression signal generation module 42 including instructions to generate expression signals from microarray data, a quality control module 44, a classification call generation module 46 and a report generation module 48. Application module 40 also includes various other modules adapted to perform various support functions, such as outlier removal and other functionality. Each module includes instructions, which when executed by one or more processors, cause the processor(s) to implement the processes as will be discussed in more detail below. It should be appreciated that application module 40, or portions thereof, as well as appropriate data can be downloaded to and executed on client system 130, analysis system 150 or other system.

Figure 2:
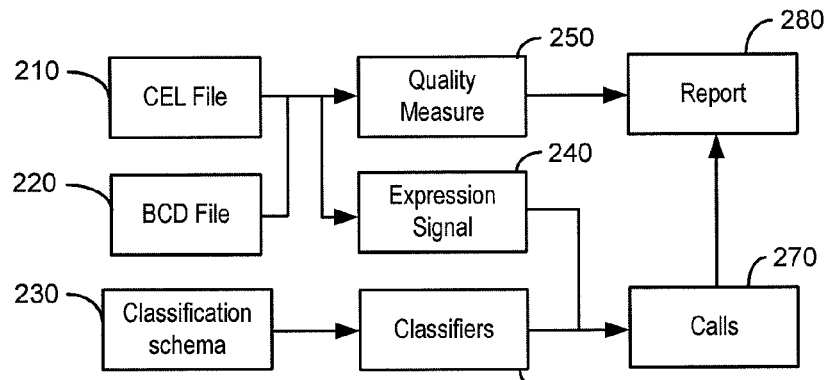
FIG. 2 illustrates a general overview of a classification and reporting process implemented by application according to one embodiment.

FIG. 2 illustrates a general overview of a classification and reporting process implemented by application 40 according to one embodiment. As shown, a microarray data file 210 is received for processing. Typically, the data file 210 includes an intensity summary and standard deviation of pixel intensities for the array. One example of such a file is a CEL file that contains the intensity summary, standard deviation of pixel intensities in a cell (e.g., small rectangular area where probes with the same oligonucleotide sequence are synthesized), and number of pixels per cell. A design file 220 is also received for processing. One example is a BCD file that is a binary file format that includes microarray design information. expression signal generation module 42 processes the data file 210 and the design file 220 to produce an expression signal 240 as will be discussed in more detail below. Similarly, in one embodiment, these two files are processed by quality control module 44 to determine one or more quality control measures 250 as will be discussed in more detail below. In one embodiment, a quality control measure is used as a measure of the quality of an entire array chip, and can be used to invalidate an entire array experiment. In one embodiment, classification call generation module 46 receives a classification schema 230 and processes the data according to one or more classification models to determine appropriate classification calls within the classification schema. One possible call, according to one embodiment, is an Indeterminable Call, which may result from a conflict of calls of different classification models, or which may result from a call being outside of the targets of the classification schema. A report 280 is generated and displayed, printed or otherwise used to apprise a physician or lab technician of the analysis results.

Expression Signal Generation

According to one embodiment, expression signals are generated by module 42 based on the analysis of a data file generated by an expression array system. One example is a CEL file generated by the Affymetrix AMDS system.

In one embodiment, data for perfect match and mismatched probes are used to generate signals. Regarding to the usage of perfect match (PM) probes and mismatch (MM) probes, two approaches include: (1) using only PM probes, and (2) using differences between PM and MM intensities. Using only PM probes leads to small variances when assay, protocol and array type do not change. Using differences between PM and MM probes leads to robust classification results when there are some changes in assay, protocol or array type. Therefore, in one embodiment, a signal PS (based on PM probes only) is used for the calculation of certain quality measures which are related to signals in a single microarray, e.g., the scaling factor, poly-A ratios, and 3' to 5' ratios. In one embodiment, a signal DQN (based on the differences of PM and MM intensities) is used for classification. The PS, DS, PQN and DQN signals were proposed in Liu, et al. (Liu, W.-m., R. Li, J. Z. Sun, J. Wang, J. Tsai, W. Wen, A. Kohlmann and P. M. Williams (2006), PQN and DQN: Algorithms for expression microarrays, J. Theoretical Biol., 243, 273-278—hereinafter "Liu 2006"), which is incorporated by reference herein. Only PS, DS and DQN signals are used in one embodiment.

Figure 3:
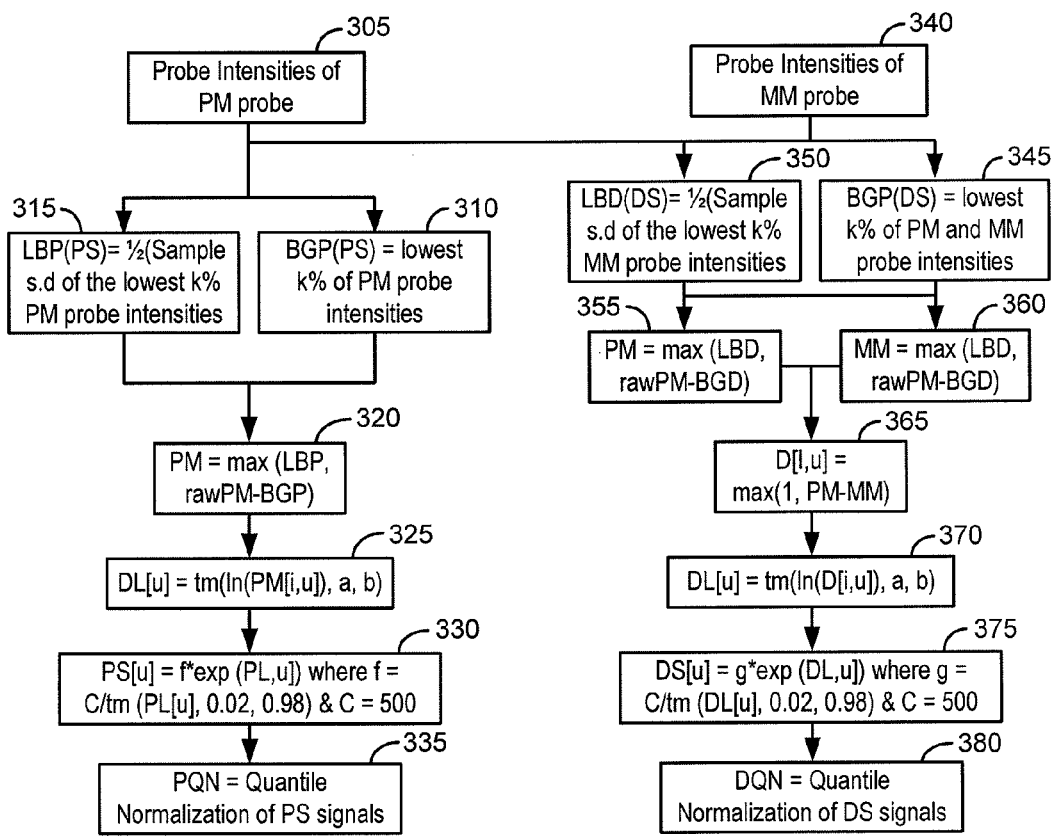
FIG. 3 is a flow chart for producing various expression signals according to one embodiment.

FIG. 3 is a flow chart for producing various expression signals according to one embodiment. Initially the probe intensities of PM and MM probes are determined in steps 305 and 340. In step 310, the background, BGP, is calculated for PS signals as the average of the lowest k % of PM probe intensities. PS signals are signals using only perfect match probes and scaled with a constant multiplier. In step 315, the lower bound, LBP, of PS signals, is determined as either 0.01 or half of the sample standard deviation of the lowest k % PM probe, whichever is larger (e.g., in most cases, it is the latter, and 0.01 is only used to avoid a close-to-zero value of LBP). In certain aspects, the parameter k is 1.2 for the AmpliChip® Human GX1 microarray and its simulation with the AmpliChip® Leukemia microarray or the U133 Plus 2.0 microarray. For old data generated with the AmpliChip® Leukemia microarray or its simulation with the U133 Plus 2.0 microarray, k=1.5 is used. For old data generated with the U133 Plus 2.0 microarray, k=2 is used. It should be appreciated that other values for k may be used.

In step 320, the adjusted PM signal for every PM cell is determined as $$PM=\max(LBP, \text{raw}PM-BGP).$$

Then, in step 325, the trimmed means of log signals between the a-quantile and b-quantile is calculated for every unit:

$$PL[u]=\text{trimmedMean}(\ln(PM[i,u]),a,b),$$

where PM[i,u] is the intensity of the i-th perfect match cell of unit u, PL[u] is the unscaled perfect match signal for unit u at log scale, and ln is the natural logarithm. For the GX1 microarray or its simulation with the AmpliChip® Leukemia microarray or the U133 Plus 2.0 microarray, a=0.15 and b=0.9. For old data generated with the AmpliChip® Leukemia array or the U133 Plus 2.0 microarrays, a=0.4 and b=0.9.

In step 330, the scaled PM signal is determined:

$$PS[u]=f^*\exp(PL[u]),$$ where the scaling factor f=C/trimmedMean(exp(PL[u]),0.02,0.98), and the constant C is set to be 500.

In step 335, the quantile normalized PS signal is determined. Some existing algorithms use the average quantiles of a set of microarrays under study, however, this is disadvantageous as the signal obtained from the same microarray can be different if it is included in different study sets. The quantile normalization technique described herein, in certain aspects, uses a theoretical distribution (beta distribution) or the empirical distribution from a predefined set of high quality microarrays (they do not change for different study groups); therefore, this approach advantageously generates signals that are independent of other arrays in the same study.

In step 345, the background, BGD, for DS signals is calculated as the average of the lowest k % of PM and MM probe intensities. DS signals are signals based on the differences between intensities of PM probes and intensities of MM probes; they can be scaled with a constant multiplier. In step 350, the lower bound, LBD, of DS signals, is determined as either 0.01 or half of the sample standard deviation of the lowest k % PM and MM probe intensities, whichever is larger. The parameter k is 1.2 for the AmpliChip® Human GX1 microarray and its simulation with the AmpliChip® Leukemia microarray or the U133 Plus 2.0 microarray. For old data generated with the AmpliChip® Leukemia microarray or its simulation with the U133 Plus 2.0 microarray, k=1.5 is used. For old data generated with the U133 Plus 2.0 microarray, k=2 is used. It should be appreciated that other values for k may be used.

In steps 355 and 360, the adjusted PM and MM signals for every probe pair are determined as:

$$PM=\max(LBD, \text{raw}PM-BGD), \text{ and}$$

$$MM=\max(LBD, \text{raw}MM-BGD).$$

In step 365, the adjusted difference is determined as:

$$D=\max(1, PM-MM).$$

The adjusted difference between PM and MM of the i-th probe pair in unit u is denoted by D[i, u]. In step 370, the unscaled difference signal for unit u at log scale is determined as:

$$DL[u]=\text{trimmedMean}(\ln(D[i,u]),a,b).$$

For the GX1 microarray or its simulation with the AmpliChip® Leukemia microarray or the U133 Plus 2.0 microarray, a=0.15 and b=0.9. For old data generated with the AmpliChip® Leukemia array or the U133 Plus 2.0 microarray, a=0.4 and b=0.9. In step 275, the DS signal is determined as:

$$DS[u]=g*\exp(DL[u]),$$

where the scaling factor g=C/trimmedMean(exp(DL[u]), 0.02, 0.98), and C=500.

In step 380, the quantile normalized DS signal (DQN) is determined. In one embodiment, the quantile normalization function is:

$$x_{norm}=F^{-1}(F_e(X)),$$

where $F_e$ is the empirical distribution function of signals X before normalization, and F is the beta distribution function. The quantiles of the beta distribution with parameters p=1.2 and q=3 are used for quantile normalization in one embodiment. The DQN signals normalized with these quantiles are denoted herein by Dn3. The basic idea of quantile normalization is to use a non-linear transformation to make the distribution of the signals the same. For example, let q[1], q[2], ..., q[n] be the quantiles of a distribution, and let the ranks of signals y[1], y[2], ..., y[n], be r[1], r[2], ..., r[n]. When there is no tie, the quantile normalized signals are q[r[1]], q[r[2]], ..., q[r[n]]. Where there are ties of the original signals, averages are taken so that the quantile normalized signals have the same values if the original signals have the same values. In certain aspects, therefore, normalizing the expression signal based on a theoretical distribution at the unit level advantageously produces a normalized expression signal for the single microarray that is independent of other microarrays.

It is possible to perform normalization for all 54336 units targeting human genes on the GX1 array. However, in certain aspects, only the signals obtained from the common part of the GX1 microarray and the AmpliChip® Leukemia microarray such as ALGX1D301 (it is a code for 1467 units where 1450 units targeting human genes use up to 5 atoms per unit, and 1438 units are used for classification) are used. In certain aspects, four units for housekeeping genes are not used in normalization, and eight units with low signal variations are only used in normalization, but not in classification. Four of the eight units are on the U133A microarray (also on the U133 Plus 2.0 microarray), and the other four are on the U133B microarray (also on the U133 Plus 2.0 microarray). Table 1 lists these 8 probe sets.

TABLE 1

Units with Low Signal Variations

| GX1_ID | Affymetrix_ID | AorB | ExpressionLevel |
|---|---|---|---|
| R000044_n5_at | 200007_at | A | high |
| R005552_n5_at | 206014_at | A | low |
| R008382_n5_at | 208904_s_at | A | high |
| R016390_n3_at | 217181_at | A | low |
| R022629_n5_at | 222976_s_at | B | high |
| R034451_n5_at | 234873_x_at | B | high |
| R036545_n5_at | 236967_at | B | low |
| R040371_n3_at | 240794_at | B | low |

Note that R000044_n5 (200007_at) is also on U133B, but it is only used for the part of U133A.

In one embodiment, the following two types of DQN signals are produced for classification models: Dn3_1438 and Dn3AB_1322. Note that the numbers of units may vary for different designs. The numbers used in this example are applicable to designs ALGX1D300, ALGX1D301, ALGX1D302 and ALGX1D305. For ALGX1D303 and ALGX1D306, the numbers may be different.

Dn3_1438

The code 3 after Dn indicates that the quantiles of beta distribution with parameters p=1.2 and q=3 are used for normalization. This set of signals is obtained with quantile normalization of the 1446 units (not including units for spike-in controls and housekeeping genes), 8 of them are not used for classification, and the remaining 1438 units are used for classification.

Dn3AB_1322

The letters AB indicates that the quantile normalization is performed for two subsets, one is for the units on U133A microarray and the other is for the units on U133B microarray. This special normalization method is for classifiers formed with training datasets on U133 Plus 2.0 microarrays and on the pairs of U133A and U133B microarrays. The number 1322 indicates that there are 1322 units for classification (900 units on U133A and 422 units on U133B). There are 4 more units on U133A and 4 more units on U133B for normalization but not for classification. That is, in certain aspects, the quantile normalization is done for 900+4=904 units on U133A and for 422+4=426 units on U133B separately.

Detection Calls, p-Values and Discrimination Scores

In one embodiment, detection calls (e.g., present, marginally present, or absent), p-values for detection calls, and discrimination scores are calculated but are not used for classification. The detection calls and p-values for detection calls are described in Liu, W.-m., R. Mei, X. Di, T. B. Ryder, E. Hubbell, S. Dee, T. A. Webster, C. A. Harrington, M.-h. Ho, J. Baid and S. P. Smeekens (2002), Analysis of High-Density Expression Microarrays With Signed-Rank Call Algorithms, Bioinformatics, 18, 1593-1599, which is hereby incorporated by reference herein. In certain aspects, the discrimination score of a probe pair is defined to be:

$$S=(rawPM-rawMM)/(rawPM+rawMM).$$

For a probe set, the discrimination score is the $65^{th}$ percentile of discrimination scores of all probe pairs.

Let S[i, u] be the discrimination score of the i-th probe pair of unit u. In certain aspects, a one-sided signed rank test is applied to S[i, u] for i=1, ..., N[u], where N[u] is the number of unsaturated atoms in unit u. An atom is saturated if the intensity of its mismatch probe is larger than or equal to a threshold (e.g., 65000). If all atoms are saturated, the detection call is N (i.e., no call). But for current scanners, saturated atoms are seldom detected. Therefore, in most cases, N[u] is the same as the number of atoms A[u] in a unit. The test is for the null hypothesis $$H_0:S[i,u]=\tau$$

versus the alternative hypothesis $$H_a:S[i,u]>\tau.$$

Note that u is fixed and τ=0.015. The p-value is defined to be:

$$p[u]=\operatorname{Prob}[W>W_O]+0.5*\operatorname{Prob}[W=W_O],\text{ where W is}$$
the sum of Wilcoxon signed ranks and $W_O$ is the observed sum of Wilcoxon signed ranks.

In one embodiment, two parameters $\alpha_1$ and $\alpha_2$ ($0<\alpha_1<\alpha_2<0.5$) are used to make the detection call. When $p[u]<\alpha_1$, the detection call is P (i.e., present); when $p[u]>=\alpha_2$, the detection call is A (i.e., absent); otherwise, the detection call is M (i.e., marginally present). The parameters $\alpha_1$ and $\alpha_2$ are dependent on the majority number of atoms per unit. For example, for ALGX1D301 or its simulation with U133 Plus 2.0 microarray or AmpliChip® Leukemia microarray, the majority number of atoms per unit is 5. For U133 Plus 2.0 microarray and AmpliChip® Leukemia microarray this number is 11. Table 2. lists examples of values of parameters $\alpha_1$ and $\alpha_2$.

TABLE 2

Values of $\alpha_1$ and $\alpha_2$ for Detection Calls

| Majority nAtoms/unit | α1 | α2 |
|---|---|---|
| 1 to 4 | 0.1 | 0.2 |
| 5 to 8 | 0.065 | 0.09 |
| 9 | 0.065 | 0.085 |
| 10 or 11 | 0.05 | 0.065 |
| 12 or more | 0.04 | 0.06 |

Quality Control

In one embodiment, various quality control measures are calculated in QC module 44. It should be noted that there exist quality measures that cannot be calculated with microarray data, for example, the cRNA yield. Also, all cutoff values for quality measures mentioned herein can vary. If a quality measure is not in the acceptable range, the final classification result can be reported as No Call. Some quantities are calculated and can be reported, but are not used to make No Calls. In one embodiment, a quality control measure is used to invalidate the entire array experiment.

Figure 4:
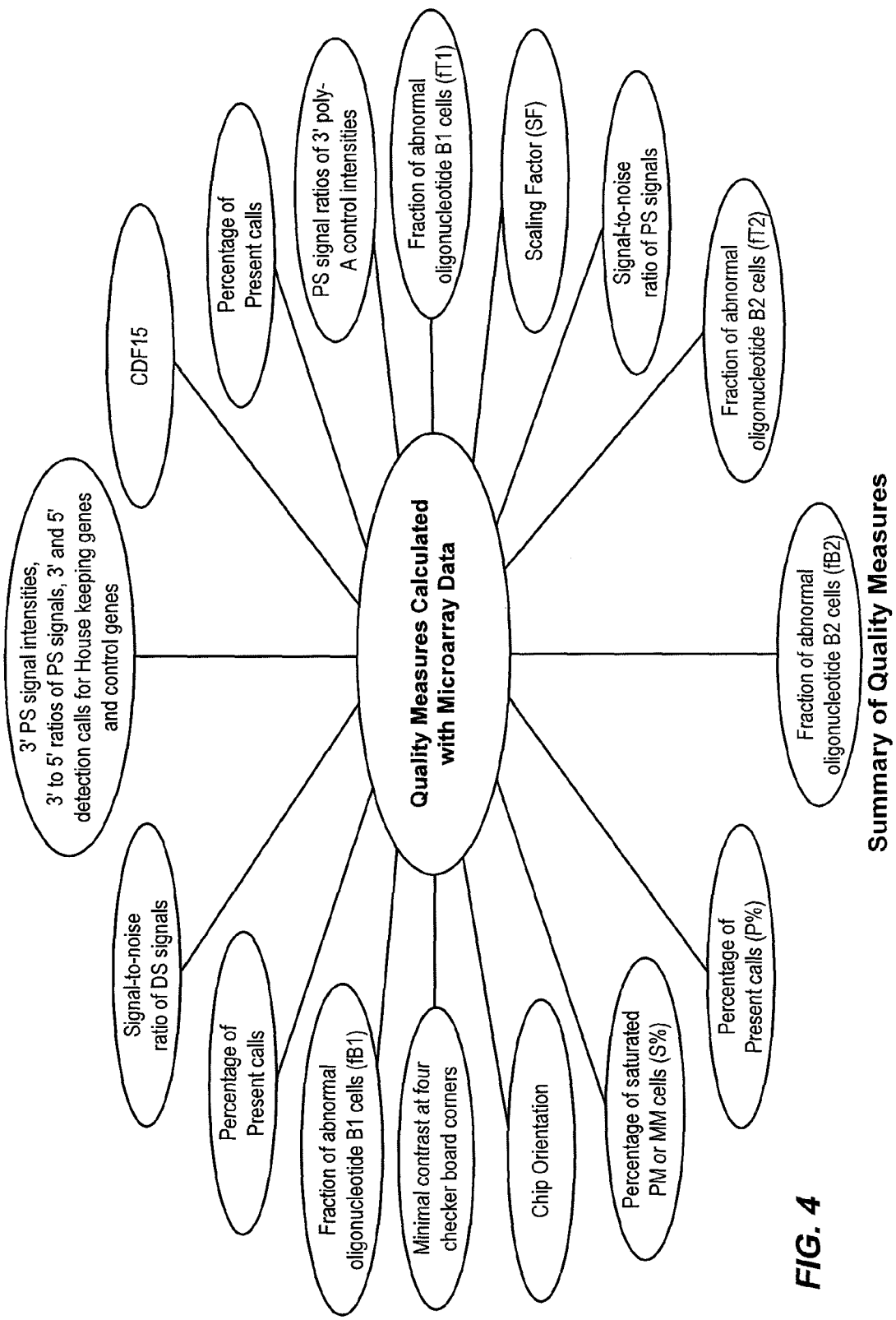
FIG. 4 illustrates quality control measures calculated from the microarray data according to various embodiments.

In one embodiment, one or more of the following quality control measures are calculated from the microarray data as shown in FIG. 4:

Scaling factor (SF), a constant (with default value of 500) divided by the trimmed mean of PS signals between 0.02 and 0.98 quantiles. When the average intensity of an array is low, SF is large. In certain aspects, SF<=15 is acceptable for GX1 microarray and its simulation with U133 Plus 2.0 microarray or AmpliChip® Leukemia microarray. For old data of U133 Plus 2.0 microarray, SF<=20 is used. For old data of AmpliChip® Leukemia microarray, SF<=10 is used.

Percentage of present calls (P %). In certain aspects, P %>=30% (35% for UHR) is acceptable for GX1 microarray and its simulation with U133 Plus 2.0 microarray or AmpliChip® Leukemia microarray. For old data of U133 Plus 2.0 microarray and AmpliChip® Leukemia microarray, P %>=20% (25% for UHR) is used.

Percentage of saturated PM or MM cells (S %). For current scanners with 16-bit unsigned integer output, a cell with intensity higher than or equal to 65000 is called saturated. For old scanners with 15.5-bit unsigned integer output, a cell with intensity higher than or equal to 46000 is called saturated. An example of an acceptable range is S %<=0.05%.

B1B2 Boundary The boundary between the intensities of oligonucleotide B1 cells and the intensities of oligonucleotide B2 cells. B1B2 boundary, in certain aspects, is defined as the geometric mean of the median of oligonucleotide B1 intensities and median of oligonucleotide B2 intensities at the four corners. For GX1 assay, the oligonucleotide B1 is spiked, and the cells for oligonucleotide B1 should be bright and the cells for oligonucleotide B2 should be dim.

fB1 Fraction The fraction, fB1, of abnormal oligonucleotide B1 cells whose intensities are on the side of oligonucleotide B2 of the B1B2 boundary. An example of an acceptable range is fB1<=0.1.

fB2 Fraction The fraction, fB2, of abnormal oligonucleotide B2 cells whose intensities are on the side of oligonucleotide B1 of the B1B2 boundary. An example of an acceptable range is fB2<=0.1.

fT1 The fraction, fT1, of abnormal oligonucleotide B1 cells in the text area of the microarray. An example of an acceptable range is fT1<=0.15.

fT2 The fraction, fT2, of abnormal oligonucleotide B2 cells in the text area of the microarray. An example of an acceptable range is fT2<=0.15.

Chip Orientation The detected orientation is one of four integers, 0, 1, 2, or 3. It indicates the multiple of 90 degrees of rotation from the regular orientation in the counter-clock-wise direction. A value different from 0 means wrong orientation. The algorithm first sets the initial value to 0. When fT1>0.15 or fT2>0.15, for example, the rotated text area is used to see whether both conditions fT1<=0.15 and fT2<=0.15 are true after the rotation. If these conditions are true after a rotation, the detected orientation is set as the positive number for that rotation.

PS Signal Ratio The PS signal ratios of 3' poly-A control intensities: PHE/LYS, THR/LYS and DAP/LYS. An example of an acceptable range is that all three conditions: PHE/LYS>=1, THR/LYS>=1, and DAP/LYS>=1.35 are true. Since these conditions are not directly related to call accuracy, in certain aspects, the new conditions PHE/LYS>=0.85, THR/LYS>=0.85 and DAP/LYS>=1 are used.

3' to 5' Ratio The 3' PS signal intensities, 3' to 5' ratios of PS signals, and 3' and 5' detection calls (Present/Absent) for housekeeping genes HSAC07 (beta-actin) and GAPDH, as well as control genes LYS, PHE, THR and DAP. These quantities can be reported, but not used to make No Calls.

Contrast Minimal contrasts at four checkerboard corners of intensities of cells for B1 oligonucleotide and B2 oligonucleotide.

PS S/N Signal-to-noise ratio of PS signals; defined as the ratio of the trimmed mean of PS signals between the 0.02 and 0.98 quantiles to the background BGP.

DS S/N Signal-to-noise ratio of DS signals; defined to be the ratio of the trimmed mean of DS signals between the 0.02 and 0.98 quantiles to the background BGD.

CDF15 The value of the empirical cumulative distribution function of inner cells (excluding one-layer of boundary cells) at $0.15*(\max(Ln(I))-\min(Ln(I)))+\min(Ln(I))$. This value is usually between 0.4 and 0.7; when it is extremely small, e.g., smaller than 0.1, it indicates that there are many cells with abnormal bright intensities. This quantity is typically not used to make No Calls.

In certain aspects, the QC measures on GX1 array and its simulation with U133 Plus 2.0 microarray or AmpliChip® Leukemia microarray are acceptable if all of the following conditions are satisfied: SF<=15, P %>=30% (35% for UHR), S %<=0.05, fB1<=0.1, fB2<=0.1, fT1<=0.15, fT2<=0.15, PHE/LYS>=0.85, THR/LYS>=0.85 and DAP/LYS>=1. Otherwise, a No Call should be made.

Classification

Classes

In one embodiment, the classification algorithms described herein are independent of the particular diseases. In certain aspects, a 19 class classification call schema is used; the 19 classes for this schema are listed in Table 3. The split of class 18 and class 19 is due to the differences of these specimens and calls in these two classes can be combined as a single class "None-of-the target" in the final report for 18-class classification schema. The 19-class classification schema can serve as a basic schema for other needs. For example, the Acute Leukemia Test can make the calls of the first 14 classes, and in case that a call is in one of the other classes, the Indeterminable Call can be made. For further classification into subclasses, the same algorithms can be applied.

TABLE 3

The 19 Classes in the Basic Leukemia Classification Schema

| Class Number | Class Name |
|---|---|
| 1 | Mature B-ALL with t(8;14) |
| 2 | Pro-B-ALL with t(11q23)/MLL |
| 3 | c-ALL/Pre-B-ALL with t(9;22) |
| 4 | T-ALL |
| 5 | ALL with t(12;21) |
| 6 | ALL with t(1;19) |
| 7 | ALL with hyperdiploid karyotype |
| 8 | c-ALL/Pre-B-ALL without t(9;22) |
| 9 | AML with t(8;21) |
| 10 | AML with t(15;17) |
| 11 | AML with inv(16)/t(16;16) |
| 12 | AML with t(11q23)/MLL |
| 13 | AML with normal karyotype or other abnormalities |
| 14 | AML complex aberrant karyotype |
| 15 | CLL |
| 16 | CML |
| 17 | MDS |
| 18 | None-of-the-target bone marrow |
| 19 | None-of-the-target blood |

Multi-Class Classification

There are many different ways to classify more than 2 classes. Two approaches are based on binary classifiers: one is all-pair-wise and the other is one-versus-others. The all-pair-wise approach makes calls based on the results of all possible class pairs. The one-versus-others approach makes calls based on the results of every class versus all other classes. The one-versus-others approach usually gives more indeterminable calls due to ties of the results. Therefore, in one embodiment, the all-pair-wise approach is used to make principal calls. In certain aspects, the one-versus-others approach is used to verify particular principal calls.

Classification Models, Verifiers and Voting Procedures

In one embodiment, a classification model is defined as a set of linear classifiers for all class pairs (for the all-pair-wise approach), or a set of linear classifiers for all classes (for the one-versus-others approach). In certain aspects, the latter is only used as a verifier. A verifier is a classification model used to verify whether its call is consistent with the candidate call made by other classification models.

Figure 5:
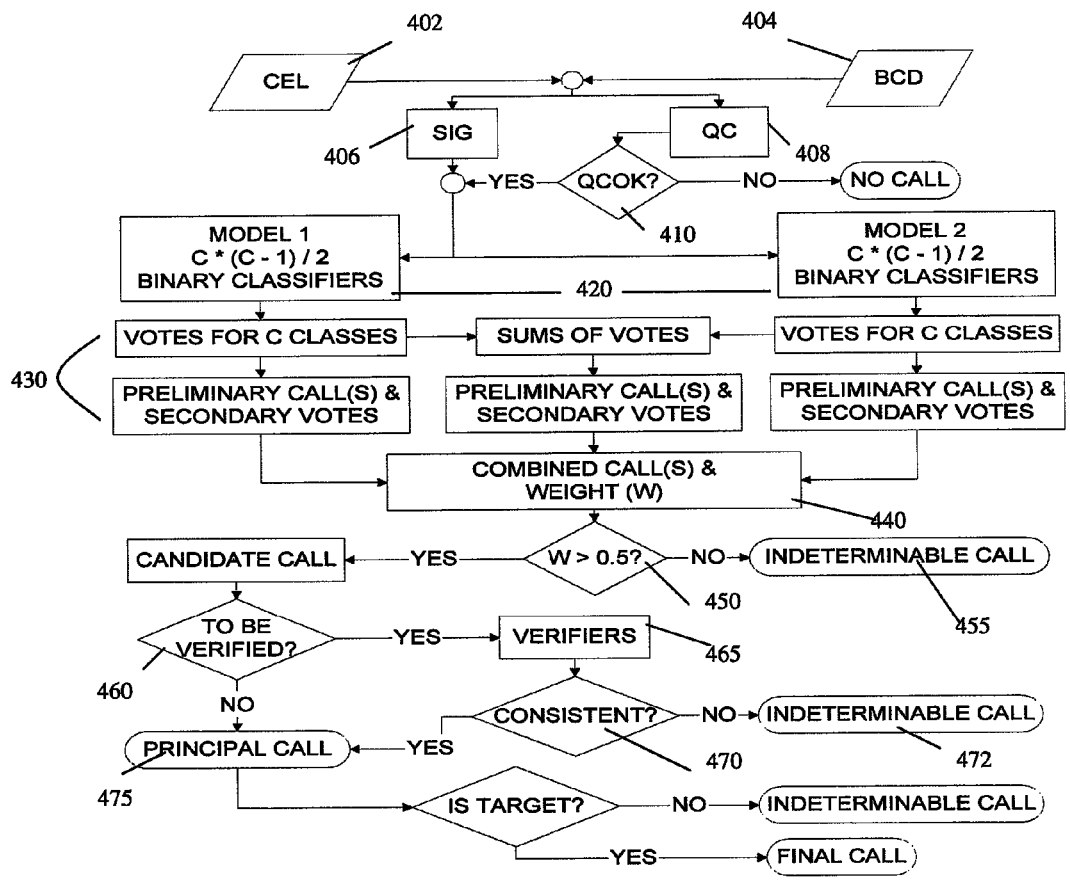
FIG. 5 illustrates the work flow of a classification process according to one embodiment.

The work flow of a classification approach according to one embodiment is shown in FIG. 5. Initially, the CEL file(s) 210 is received at step 402 and the BCD file 220 is received in step 404. Expression signals (SIG) are generated in module 42 as described above in step 406, and quality control module 44 processes the data as described above in step 408. In decision step 410, if the quality control module detects that a measurement is out of the allowed range, a NO CALL is made; if the Quality Control Module determines that all is OK, processing proceeds. Binary classifiers are determined in step 420 for each classification model. Here, all-pair-wise classifiers are described. For example, if there are C=19 classes, there are 19*(19−1)/2=171 class pairs; a classification model contains 171 binary classifiers. Let n be the number of variables (probe sets). For example, n=1322 for signals Dn3AB_1322, and n=1438 for signals Dn3_1438. The classifier for class pair (i, j) (where 1<=i≤j<=C) has (n+1) coefficients, w[0; i, j], w[1; i, j], . . . , w[n; i, j]. Denoting the signals of a microarray by x[1], . . . , x[n], the discriminant, also known as decision function, for class pair (i, j) is:

$$f(x;i,j)=w[0;i,j]+w[1;i,j]*x[1]+ \ldots +w[n;i,j]*x[n].$$

The sign of f(x; i, j) can be 1, 0 or −1, where 1 indicates that the binary classifier is for class i with small index, −1 indicates that the binary classifier is for class j with large index, and 0 indicates a tie between the two classes. In step 430, votes for classes are determined. The votes of all classes are initialized to be 0 in certain aspects. If f(x; i, j)>0, a vote is added to class i; if f(x; i, j)<0, a vote is added to class j; if f(x; i, j)=0, 0.5 votes are added to class i and 0.5 votes are added to class j. This is repeated for all class pairs to obtain the preliminary votes for all classes. The preliminary call of the model is the class (or classes) with the maximal vote.

In one embodiment, two or more classification models are used, where the sums of preliminary votes of multiple models are used as another classification model. For example, if two classification models are used, e.g., Model 1 and Model 2 in FIG. 5, then the sums of preliminary votes of the two models become the third classification model.

In step 440 the calls are combined and a weight determined. In certain aspects, the preliminary calls of all classification models are combined using a secondary voting procedure. If the preliminary call of a classification model contains m classes, each of the m called classes has 1/m secondary votes by this model and other classes have 0 secondary votes. The secondary votes of all models are added for every class. The combined call is the class or classes with the maximal sum of secondary votes. Also, the weight of the combined call(s), i.e., the ratio of the maximal sum of secondary votes to the total secondary votes, is output. In certain aspects, the total of secondary vote is equal to the number of models including the model based on sums of votes. In decision step 450, if the weight is larger than a threshold, e.g., 0.5, then the call is unique, and the candidate call is this unique combined call. If the weight is below the threshold, e.g., 0.5 or less, the call can be either unique or not unique, and an indeterminable call is reported at step 455. In one aspect, the code −1 is used to denote the indeterminable call due to low weight of the combined call(s).

An example of a 4-class classification schema is used to illustrate the above voting procedures. Table 4. lists the signs of the decision functions for 4*(4−1)/2=6 class pairs of two classification models.

TABLE 4

Signs of Decision Functions of Two Classification Models for 6 Class Pairs of 4 Classes

| ClassPair | i | j | Model1 | Model2 |
|---|---|---|---|---|
| C1 vs C2 | 1 | 2 | −1 | −1 |
| C1 vs C3 | 1 | 3 | −1 | −1 |
| C1 vs C4 | 1 | 4 | 0 | 1 |
| C2 vs C3 | 2 | 3 | 1 | 1 |
| C2 vs C4 | 2 | 4 | 1 | −1 |
| C3 vs C4 | 3 | 4 | 1 | 1 |

Table 5. lists the preliminary votes of the two models and the sums of votes which form the third classification model.

TABLE 5

Votes of Two Models and Sums of Votes

| Class | Model1 | Model2 | SumsOfVotes |
|---|---|---|---|
| C1 | 0.5 | 1 | 1.5 |
| C2 | 3 | 2 | 5 |
| C3 | 2 | 2 | 4 |
| C4 | 0.5 | 1 | 1.5 |

The preliminary call of model 1 is class 2. Therefore, for model 1, class 2 has secondary vote 1, and other classes have secondary vote 0. The preliminary call of model 2 is classes 2 and 3. Therefore, for model 2, classes 2 and 3 have secondary vote 0.5 and other classes have secondary vote 0. The preliminary call of the model based on the sums of votes is class 2. Table 6. lists the secondary votes (weights of the preliminary calls) for three models including the model based on sums of preliminary votes and the total secondary votes for every class.

TABLE 6

Secondary Votes of Three Models and the Total Secondary Votes for Every Class

| Class | Model1 | Model2 | SumsOfVotes | TotalSecondaryVotes |
|---|---|---|---|---|
| C1 | 0 | 0 | 0 | 0 |
| C2 | 1 | 0.5 | 1 | 2.5 |
| C3 | 0 | 0.5 | 0 | 0.5 |
| C4 | 0 | 0 | 0 | 0 |

Since class 2 has the maximal secondary vote 2.5, the combined call is a call for class 2 with weight 2.5/(2.5+0.5)=2/3=0.8333. Since this weight is larger the threshold, 0.5, the candidate call is the same as the combined call, i.e., the call for class 2.

A determination is made in step 460 as to whether the Candidate call needs to be verified. If the candidate call is one of the calls that should be verified, one or more verifiers can be applied at step 465. A determination of consistency is made at step 470: if the candidate call is consistent with the calls of the verifiers, then the principal call is the same as the candidate call. If the candidate call is inconsistent with the call of a verifier, an indeterminable call is reported at step 472. In one aspect, the indeterminable call caused by a verifier is coded with a negative number with four digits, e.g., −ABCD. Here, the last two digits, CD, denote the candidate call (e.g., 02 for the candidate call of class 2), the first digit, A, is the one-based index of the verifier, and the second digit, B, is 1 if the verifier is all-pair-wise, and is 2 if the verifier is one-versus-others.

If the candidate call is not one of the calls that should be verified, it is taken as the principal call at step 475. One reason verifiers are not applied to all classes is to avoid making many correct candidate calls as indeterminable calls.

In one embodiment, two verifiers are used for 19-class classification schema. The first verifier is an all-pair-wise classification model for 7 major classes (e.g., ALL, AML, CLL, CML, MDS, none-of-the-target bone marrow, and none-of-the-target blood). If the candidate call is a class of ALL, MDS or none-of-the-target bone marrow, this verifier is to be applied. The second verifier is a one-versus-others classification model for 8 classes in ALL. It is applied to the first 7 ALL classes. It only uses the result of a single class versus other classes. For example, if the candidate call is for class 2, the binary classifier of class 2 versus the union of classes 1, 3, 4, 5, 6, 7 and 8 is used to check whether this binary classifier supports the call for class 2.

In certain aspects, a classification model can be used for a subset of the original targets. For example, the 19-class classification model can be used for the 14-class ALL/AML classification. If a call is not one of the 14 target classes, an indeterminable call can be reported. If a call is one of the 14 target classes, then the principal call becomes the final call.

It should be understood that a classification scheme with any number of classes may be used.

Confidence Measures of Classification
Weight of Maximal Secondary Vote

As defined above, the weight of a maximal secondary vote is equal to the quotient of the maximal secondary vote divided by the number of models (total secondary votes). It is a number between 0 and 1 and can be considered as a confidence measure of classification. In one aspect, when the weight of maximal secondary vote is 0.5 or less, an indeterminable call is reported. It should be appreciated that the threshold value may be different than 0.5, e.g., it may be between 0.4 and 0.6 or even between 0.25 and 0.75.

Minimal Confidence Score Simulating Probability of Logistic Models

In one embodiment, the coefficients of the binary linear classifier for class pair $(i, j)$ ($1<=i<j<=C$) are normalized. for example, the coefficients $w[0; i, j]$, $w[1; i, j]$, $w[n; i, j]$ are divided by $w=sqrt(sum(w[1; i, j]^2+w[n; i, j]^2))$. For simplicity, $w[0; i, j]$, $w[1; i, j]$, $w[n; i, j]$ is used to denote the normalized coefficients. After normalization, the decision function $f(x; i, j)=w[0; i, j]+w[1; i, j]*x[1]+ \ldots +w[n; i, j]*x[n]$ becomes the signed distance to the separator of class i and class j, and it is also the projection of the data point x onto the line perpendicular to the separator of the two classes.

The linear classifier for class pair $(i, j)$ can be regarded as a logistic model:

$$Log(P[i,j]/(1-P[i,j]))=(w[0; i,j]+w[1; i,j]*x[1]+ \ldots + w[n;i,j]*x[n])/d(i,j)=z[i,j].$$

The denominator $d(i, j)$ is set as the average of two numbers, where one number is the minimal positive projection of training data of class i onto the line perpendicular to the separator of class pair $(i, j)$, and the other number is the minimal absolute value of negative projection of training data of class j onto the same line. A small class index corresponds to the positive direction of the line perpendicular to the separator.

The probability $P[i, j]$ of class i conditioned on class pair $(i, j)$ can be calculated as $$P[i,j]=exp(z[i,j])/(1+exp(z[i,j])), \text{ if } i<j, \text{ or}$$

$$P[i,j]=exp(-z[j,i])/(1+exp(-z[j,i])), \text{ if } i>j.$$

If the combined call is class i, for all possible class pairs $(i, j)$ ($j=1, \ldots, C$, and $j!=i$), the minimal probability is calculated where $z[i, j]$ (for $i<j$) or $z[j, i]$ (for $i>j$) is in favor of class i. In other words, $$P[i]=min(P[i,j]; j=1, \ldots, C, j!=i \text{ and } P[i,j]>=0.5)$$

is defined as the minimal confidence probability of all class pairs that are in favor of class i.

In certain aspects, $d[i, j]$ is set equal to 1 for all class pairs, e.g., using the signed distance (without considering the worst correctly called training data) to calculate $P[i, j]$ and $P[i]$. For clarity, the score calculated with setting $d[i, j]=1$ is denoted by $P_1[i]$. Both $P[i]$ and $P_1[i]$ are reported.

Supporting Tools

Selection of Units

In one embodiment, when the expression signals of available units such as Dn3_1438 are used, all 1438 units need not be used for every class pairs with the all-pair-wise approach, or for every class with the one-versus-others approach. In one aspect, a procedure to select the top N[i, j] units with the maximal absolute values of t-statistic for class pair (i, j) is used: a t-statistic based on equal variance assumption is used because it does not introduce additional complexity of variant degrees of freedom and the results are similar to the results using unequal variance assumption. The number N[i, j] of selected units is determined by the classification difficulty level of the class pair. In one embodiment, the maximal relative information gain (RIG), which is a number between 0 and 1, is used to define the difficulty level for classification. For example, if the relative information gain of a unit is 1, then the expression signal of this unit can perfectly separate the class pair. If the maximal relative information gain of a class pair for all units is more than 0.9, it is an easy-to-classify class pair, and a small number of units, e.g., N[i, j]=350 is selected. If the maximal relative information gain of a class pair is 0.9 or less, it is a difficult-to-classify class pair, and a large number of units, e.g., N[i, j]=1280 is selected. Applying this rule to 19 classes, 147 easy-to-classify class pairs and 24 difficult-to-classify class pairs were found for the training dataset with 1922 CEL files, and they remain unchanged for three 30-fold cross validations.

In the following, the relative information gain for a unit is defined. Let x[i, 1], x[i, 2], . . . , x[i, m] be the normalized expression signals of m CEL files in class i for a particular unit, and x[j, 1], x[j, 2], . . . , x[j, n] be the normalized expression signals of n CEL files in class j for the same unit. The entropy of the class pair (i, j) for the particular unit across N=(m+n) CEL files is:

$$E(m,n) = -p_1 * \log_2(p_1) - p_2 * \log_2(p_2),$$

where $p_1 = m/N$, $p_2 = n/N = 1 - p_1$, $\log_2$ is the logarithmic function of base 2. If $p=0$, $p * \log_2(p)$ is defined to be 0. The entropy of the class pair for this unit is a number between 0 and 1. Consider a separation value s. Assume that for class i there are c CEL files with expression signals smaller than s, and (m–c) patients with expression signals larger than s. Also assume that for class j there are d CEL files with expression signals smaller than s, and (n–d) patients with expression signals larger than s. Then the entropy of the class pair separated by the value s is the weighted average of the entropies of the two pairs of subsets:

$$E(m,n,c,d) = ((c+d)/N) * E(c,d) + ((N-c-d)/N) * E(m-c, n-d).$$

The information gain (see, e.g., Mitchell, M. (1997) Machine Learning, McGraw-Hill, N.Y.) for the separation value s is defined as $$G(s) = E(m,n) - E(m,n,c,d).$$

Note that for the class pair, E(m, n, c, d) is a number between 0 and E(m,n) and thus G(s) is a number between 0 and E(m,n) which is no more than 1. If s gives a perfect separation, i.e., c=m and d=0, or c=0 and d=n, then E(m, n, c, d)=0, but it is not possible to tell this situation if only the value of G(s) is known.

The relative information gain is defined as:

$$R(s) = G(s)/E(m,n) = 1 - [E(m,n,c,d)/E(m,n)].$$

The RIG is a number between 0 and 1, and it is 1 if and only if E(m, n, c, d)=0, i.e., the value s can perfectly separate the two classes.

Making Linear Classifiers

There are many different ways to make linear classifiers. In one embodiment, the R program pwmain.r that calls pwsub.r is implemented to make linear classifiers. The program calls the R package e1071 (see, e.g., Meyer, D. (2007) Support vector machines: The interface to libsvm in package e1071, cran.r-project.org/web/packages/e1071/index/html) with an interface to the LIBSVM software library (see, e.g., Chang, C.-C. and Lin, C.-J. (2001) LIBSVM: a library for support vector machines, www.csie.ntu.edu.tw/~cjlin/libsym) for support vector machines (Cortus, C. and Vapnik, V. (1995) Support vector networks, Machine Learning, 20, pp. 1-25; Vapnik, V. (1999) The Nature of Statistical Learning Theory (second edition), Springer, N.Y.; and Scholkopf, B. and Smola, A. J. (2002), Learning with Kernels: Support Vector Machines, Regularization, Optimization and Beyond, MIT Press, Cambridge, Mass., which are each hereby incorporated by reference herein) with linear kernel. For example, let mdXIJ be the matrix of expression signals of class pair (i, j) with n columns (for units) and (nI+nJ) rows (for CEL files, the first nI rows for CEL files in class I and the next nJ rows for CEL files in class J). The following lines of code provide the vector vdW of length (n+1) for the constant and coefficients of the binary classifier for class pair (i, j). The first component vdW[1] is the constant term w[0; i, j] and the remaining components vdW[2:(n+1)] are the coefficients:

$$w[1; i,j], \ldots, w[n; i,j].$$

$$viYIJ = \text{as.factor}(c(\text{rep}(0, nI), \text{rep}(1, nJ)));$$

$$svmIJ = svm(mdXIJ, viYIJ, \text{kernel} = \text{"linear"}, \text{cost} = 1, \text{scale} = \text{FALSE});$$

$$vdW[1] = -svmIJ\$rho;$$

$$vdW[2:(n+1)] = t(svmIJ\$coefs) \%*\% svmU\$SV;$$

It is possible to scale mdXIJ and then scale vdW accordingly, however, the details can be found in the program pwsub.r.

Projection Plot

In one embodiment, a projection plot is provided for data visualization. A projection plot is a visualization tool for plotting the projections of training and testing data points on the lines perpendicular to the separators of class pair. The projections are also the normalized decision functions mentioned above. The signs of projections determine the votes. For 19 classes, it is difficult to show and comprehend plots for all 171 class pairs. Therefore, if the reference standard of the testing data is in class 9 (when reference standard is not available, the call of the classification models is used), 18 class pairs including class 9 as a pair member are plotted, and class 9 in this case is called the class of interest. In certain aspects, the user can choose another class as the class of interest. Therefore, the plots for all 171 class pairs can be shown in multiple plots for different 18 class pairs.

Figure 6:
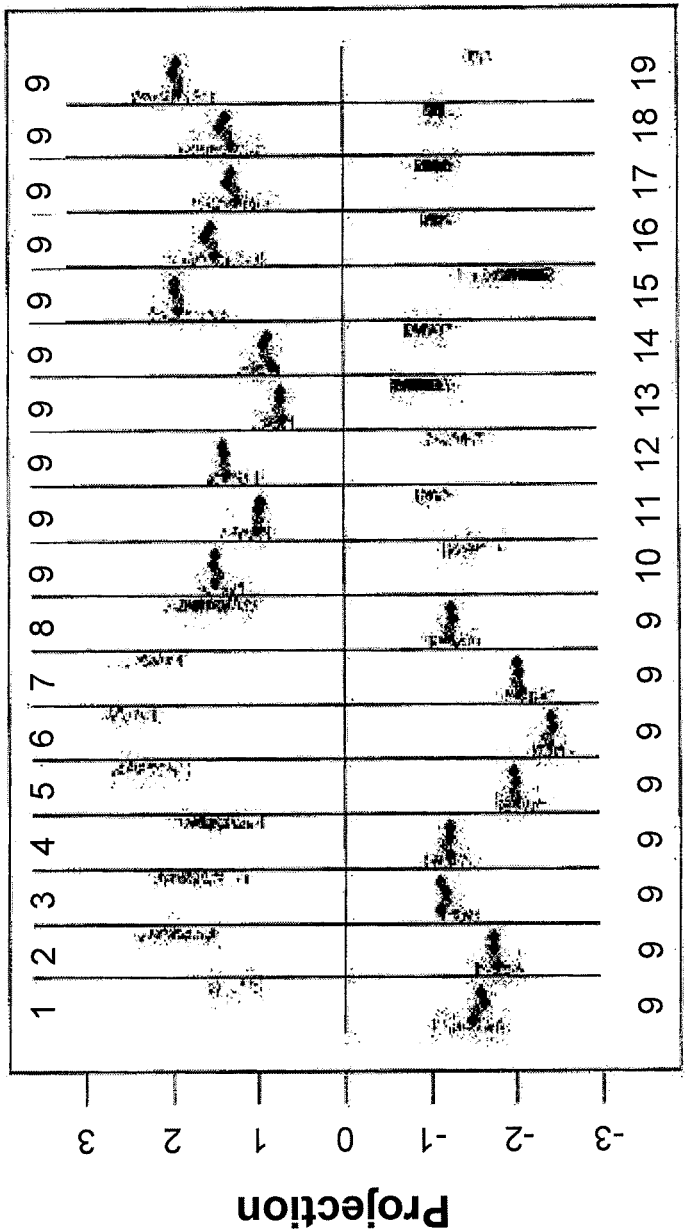
FIG. 6 is a projection plot of four testing data from 4 centers (MUC_00583, BAS_00052, LIN_00020 and GEN_00020) represented by red, green, blue and brown bullets.

FIG. 6 is an example of a projection plot of four testing data from 4 centers (MUC_00583, BAS_00052, LIN_00020 and GEN_00020) represented by red, green, blue and brown bullets. Class 9 (the reference standard and calls) is the class of interest. The class of interest is shown in the main title. The calls are shown in the parentheses in the subtitle. The vertical axis represents the projections on the lines perpendicular to the 18 separators. The numbers at the top and bottom of the plot represent the class pairs. The small black dots are projections of training data of class 9, and the small blue dots are projections of training data of other classes. Small random shifts in the horizontal direction are used for projections of training data to reduce overlaps of the points. It can be seen that the projections of the testing data are consistent with those of training data of class 9; they are clearly away from the separators. Therefore, they give very confident calls for class 9.

Figure 7:
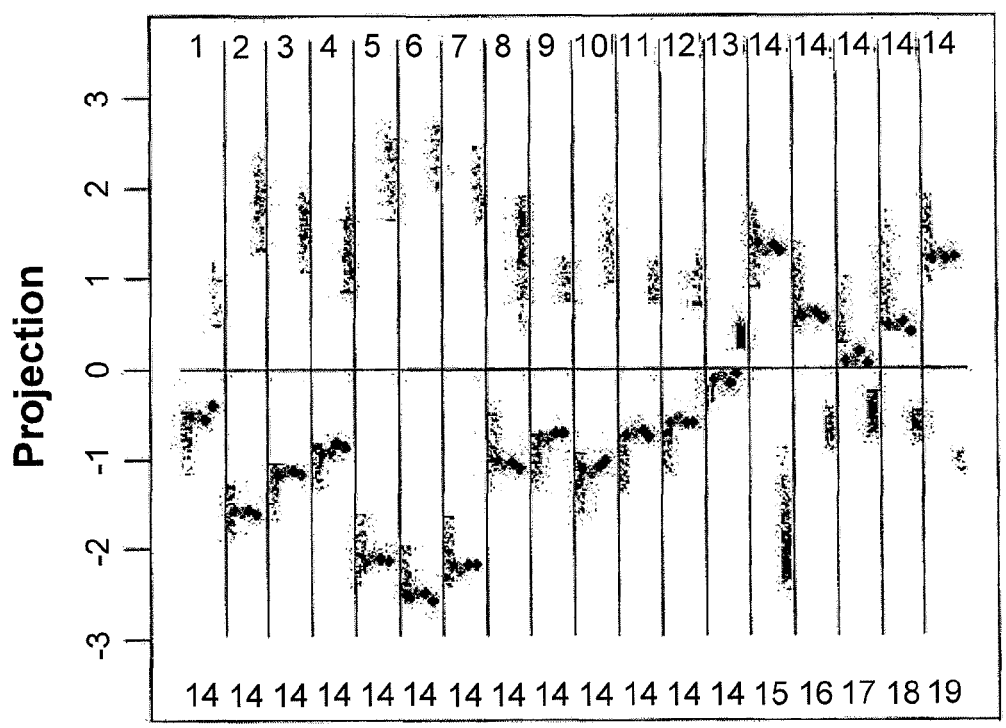
FIG. 7 is a projection plot of four testing data in class 14. The four testing data (MUC_00623, BAS_00082, LIN_00050 and GEN_00050) are in class 14.

FIG. 7 is an example of a projection plot of four testing data in class 14. The four testing data (MUC_00623, BAS_00082, LIN_00050 and GEN_00050) are in class 14. They are on the correct sides of the separators, and therefore are called class 14. However, it can be seen that for class pair (13, 14) and class pair (14, 17), the testing data are closer to the separators than the training data in class 14. Therefore the confidence of the call is low.

Outlier Detection

In one embodiment, an outlier detection process is provided for identifying statistically significant outliers within replicates so that outliers can be excluded when estimating the signal changes caused by protocol changes and their impact on call accuracy. In one embodiment, the outlier detection process is based on the median absolute deviation (MAD) of the ln(DS) signals. First, the absolute deviation is calculated for each unit in the replicate CEL files.

$$A[i,j] = |X[i,j] - m[i]|,$$

where $X[i, j]$ is the ln(DS) signal for unit i and CEL file j, $m[i]$ is the median of unit i across all replicate CEL files and $A[i, j]$ is the absolute deviation of unit i and CEL file j.

The median absolute deviation, $D[i]$, for probe set i across all replicate CEL files is then calculated as $$D[i] = \text{median}(A[i,j]).$$

Next, the proportion of probe sets producing absolute deviations larger than or equal to 5 $D[i]$ is calculated. This proportion is denoted by $F[j]$ for CEL file j. Further, the median, M, and MAD, $\Delta$, of $F[j]$ is calculated for all CEL files. If $F[k] > M + c \Delta$, CEL file k is regarded as an outlier. In one aspect, the coefficient c is selected to be 10, however, other values may be used as desired.

Assessment of Impact of Protocol Changes on Call Accuracy

In the process of development of products there are usually protocol changes. It is therefore desirable to make reliable estimations about the impact of these changes on expression signals and on call accuracy (see, e.g., Liu, W.-m., W. Wen, B. Brady, Y. Li, J. Sun, N. Tan, J. Tsai, C. J. Elkin, R. T. Kurnik, P. M. Williams and S. Lee. Assessment of Impact of Protocol Changes on Classification Accuracy, 2007 Proceedings of the Joint Statistical Meetings, American Statistical Association, Alexandria, Va., 2458-2459, which is hereby incorporated by reference). FIG. 8 shows the flow chart of an algorithm termed IASCCA (Impact of Additive Signal Changes on Call Accuracy) according to one embodiment.

To implement the IASCCA, a large number of replicates are needed, for example, 24 replicates for the new protocol and 24 replicates for the old protocol as the control. It is generally impractical to do experiments on clinical specimens that cover all target classes with such a large number of replicates. However, cell lines or UHR (Universal Human Reference RNA) can be used to do experiments with many replicates. To assess the influences of changes observed in cell line experiments to the calls of clinical specimens, the differences within the control group and the differences between the new protocol group and the control group are calculated. These differences are added to the data of clinical specimens, a renormalization is performed, the error rate due to adding differences within the control group ($E_c$) is calculated, and the error rate due to adding differences between the new protocol and the control group ($E_{tc}$) is calculated. If $E_{tc}$ is not significantly larger than $E_c$, then it can be concluded that the influences of protocol changes on call accuracy are within the range of accuracy changes due to the variations of the replicates of the controls.

To assess whether the error rate $E_{tc}$ is significantly larger than $E_c$, in one aspect, a two-sided $(1-\alpha)$ upper confidence limit is used, and $U(E_c)$ of $E_c$ for the whole data set and the class-wise data (e.g., use $\alpha = 0.05$ for the 95% confidence limit) is used. In certain aspects, when the number of observed errors is 0 or the total virtual sample size is not more than 100, the exact limit also known as the Clopper-Pearson limit is used, otherwise the Agresti-Coull limit is used. See Brown, et al. (Brown, L. D., Cai, T. T. and DasGupta, A. (2001) Interval estimation for a binomial proportion, Statistical Sciences, 16, 101-133), which is incorporated by reference, for both and other confidence limits. $E_{tc}$ is regarded as significantly larger than $E_c$ if $E_{tc}$ is larger than the upper confidence limit $U(E_c)$.

When the conclusions for different classes differ, the worst case is used. That is, if for a single class the protocol change leads to significantly larger call errors, this conclusion should be made for that protocol change.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

Appendix

Abbreviation and Definitions

The following lists abbreviations and descriptions used in this document.

| Abbreviation | Description |
| --- | --- |
| AMDS | Affymetrix 2nd Generation Operating Software for Diagnostic System - IVD Label, appropriate for use with Class III medical devices |
| BCD file | binary file format containing microarray design information |
| Block | Probe set. It consists of multiple probe pairs targeting different segments of a gene |
| BNF | binary file format for fast access of a vector of floating point numbers. This file format is used to store the quantiles of a distribution function for normalization. It can also store the expression signals. |
| BNI | binary file format for vector of integers. Used to store gold standard class information for computation of classification confidence measures |
| CEL file | Cell Intensity File that contains the intensity summary, standard deviation of pixel intensities in a cell, and number of pixels in a cell for all cells. |

-continued

| Abbreviation | Description |
|---|---|
| Cell | Feature. It is a small rectangle area, where probes with the same oligonucleotide sequence are synthesized |
| Detection Calls | Present, marginally present, or absent calls. They are determined by the p-value of the Wilcoxon signed rank test whether the discrimination scores of probe pairs are above a preset value |
| ESCAS | Evaluation of System Changes on Algorithm Stability |
| Final call | If a principal call is in one of the target classes, it becomes the final call. |
| GB | Giga byte (measurement of computer storage capacity), $10^9$ bytes |
| GCOS | GeneChip Operating System, Affymetrix Early Generation Operating Software for Microarray assays. |
| GUI | Graphical User Interface |
| GX1 | AmpliChip ® Human GX1 microarray |
| GX1D301 | An approach to organize probes into units on the GX1 microarray using up to 5 atoms per unit. |
| IASCAS | Impact of Additive Signal Changes on Algorithm Stability |
| Indeterminable Call | There are two types of the indeterminable call. One is due to the conflict of calls of different classification models. The other is due to the fact that the call is outside of the targets of a classification schema |
| MAS 5 | Affymetrix Microarray Suite 5, a package of software, or the algorithms in the package for expression microarrays. The MAS 5 expression signals are not used, but the percentage of MAS 5 present calls can be used as a quality measure. |
| Model | classification model, a set of binary classifiers for all class pairs |
| No Call | No Call is given when the microarray data fail to pass one of many required quality filters |
| PMA | Pre Market Approval |
| Preliminary Call | Call made by a single classification model |
| Principal Call | The candidate call verified by verifiers, or the candidate call that does not need verification |
| Probe Pair | A pair of perfect match cell and mismatch cell |
| Probe Set | Block. Made of several Probe Pairs, each pair interrogating a different part of a gene. |
| SML | binary file format for parameters of a set of classifiers |
| Trimmed mean (tm) | A robust average of a set of values with certain percentage of lowest values and certain percentage of highest values removed |
| Unit | One or more blocks (probe sets) targeting the same gene. In AmpliChip Leukemia, a unit consists of 1 to 3 blocks. In other expression microarrays, including AmpliChip Human Gx1 microarray, a unit consists of one block. |
| Verifier | A classification model used to verify the principal calls made by other classification models |

Mathematical Definitions

| Term | Definition |
|---|---|
| BGD | Background for the adjustment of PM, MM for the computation of D (difference in intensity) values. It is defined as the average of the lowest k % of all (PM and MM) probe intensities. k = 1.5 for AmpliChip Leukemia k = 1.2 for AmpliChip Human Gx1 The cut-off for the lowest intensities depends on the type of the microarray and the assay. |
| BGP | Background for the k adjustment of PM for the computation of P (adjusted probe intensity) values, It is defined as the average of the lowest k % of PM probe intensities k = 1.5 for AmpliChip Leukemia k = 1.2 for AmpliChip Human Gx1. The cut-off for the lowest intensities depends on the type of the microarray and the assay. |
| D | Non-central trimmed mean of Differences between perfect match (PM) and mis-match (MM) probe intensities of the expression level (also called signal) produced by this algorithm. It is used for producing DS and DQN signals. $D = \max(1, PM - MM)$, where PM and MM are raw intensities of perfect match and mismatch signals |
| Discrimination Score, R | $(PM - MM)/(PM + MM)$, where PM and MM are raw intensities of perfect match and mismatch signals |
| DL[u] | A trimmed mean of D values at log scale used as the unscaled difference in intensities for unit u For example, a trimmed mean of log signals between the (100A)-th and (100B)-th percentiles for unit u is: $DL[u] = \text{trimmedMean}(\ln(D[n, u]), A\ B)$ where n denotes n-th probe pair in the unit u. A = 0.4 and B = 0.9 for AmpliChip Leukemia microarray, and A = 0.15 and B = 0.9 for Human GX1 microarray |

-continued

| Term | Definition |
|---|---|
| DQN | Quantile normalized DS signal. For unit u, DS[u] = g * exp(DL[u]). It is a non-central trimmed mean value that has been adjusted for the background and scaled by a chip-specific Scaling Factor, g. |
| DS | Constant Scaled D signal. For unit u, DS[u] = g * exp(DL[u]). It is a non-central trimmed mean value that has been adjusted for the background and scaled by a chip-specific Scaling Factor, g. |
| f (i, j) | Discrimination score for class pair (i, j), where i < j. f(i, j) = Σ w[m; i, j] * x[m], where m ranges from zero to the number of probe sets in the Model and x[0] is 1. |
| fT1 | Fraction of abnormal oligonucleotide B1 cells in the text area of the microarray |
| fB1 | Fraction of abnormal oligonucleotide B1 cells in the corner and the boundary areas of the microarray |
| fB2 | Fraction of abnormal oligonucleotide B2 cells in the corner and the boundary areas of the microarray |
| fT2 | Fraction of abnormal oligonucleotide B2 cells in the text area of the microarray |
| LBD | Lower bound for DS signals. It is half of the sample standard deviation of the lowest k % PM and MM probe intensities, or 0.01, whichever is larger. The cut-off for the lowest intensities depends on the type of the microarray and the assay. |
| LBP | Lower bound for PS signals. It is half of the sample standard deviation of the lowest k PM probe intensities, or 0.01, whichever is larger. The cut-off for the lowest intensities depends on the type of the microarray and the assay. |
| MM | Mis-match probe or its signal intensity, MM = max (LBD, rawMM − BGD) |
| P[i, j] | Probability of class i conditioned on class pair (i, j) in a logistic model of a linear classifier f(i, j) |
| PL[u] | A trimmed mean of PM values at log scale used as the unscaled perfect match signal for unit u. units blocks is used For example, a trimmed mean of log signals between the $a^{th}$ and $b^{th}$ percentiles for unit u is: PL[u] = trimmedMean(ln(PM[i, u]), a, b), where i denotes the i-th probe pair in the unit u<br>For AmpliChip Leukemia and HG-U133 Plus 2 microarray, a = 0.4 and b = 0.9<br>For Human GX1 microarray, we use a = 0.15 and b = 0.9. |
| PM | Perfect Match or its intensity signal.<br>For the computation of DS value, PM = max(LBD, rawPM − BGD).<br>For the computation of PS value of unit u, PM[v, u] = max (LGP, raw PM − BGP) where v denote the v-th cell in the unit u. PM signals are used to generate DS signals |
| PQN | Quantile normalized PS signal based on each calling Model |
| PS[u] | Non-central trimmed mean intensity of unit u that has been adjusted for the background adjusted PM intensities followed by and scaled by a scaling. It factor. PS[u] is used to calculate Quality Control parameters such as the 3' to 5' ratios and poly-A ratios. The scaling factor of PS signals, f, is also used as a quality measure.<br>PS[u] = f * exp(PL[u]) |
| Quantile Normalization | $x_{norm} = F^{-1}(F_e(X))$, where $F_e$ is the empirical distribution function of signals X before normalization, and F is the beta distribution function |
| Scaling factor | Two different scaling factors, f and g, are used for a microarray.<br>For PS signals, the scaling factor f for the trimmed mean of exp(PL[u]) between the $2^{nd}$ percentile and $98^{th}$ percentile is:<br>f = C/trimmedMean(exp(PL[u]), 0.02, 0.98),<br>and C = 500.<br>For DS signals, the scaling factor g for the trimmed mean of exp(DL[u]) between the $2^{nd}$ percentile and $98^{th}$ percentile is:<br>g = C/trimmedMean(exp(DL[u]), 0.02, 0.98), and C = 500. |
| Tau value | An empirically determined small threshold value between 0 and 1, that is associated with Discrimination Score of a Probe Pair. The default tau value is 0.015. |
| u | Unit, One or more blocks (probe sets) targeting the same gene |
| w(i,, j) | linear weighting factor in classification decision function for each probe set for the pairwise comparison of classes i and j. |

What is claimed is:

1. A computer implemented method of automatically classifying microarray data of a patient sample, the method comprising:

receiving microarray data representing a plurality of probes on a microarray;

automatically generating a plurality of expression signals based on the microarray data;

applying, by a computer system, a first classification model for a classification scheme having a plurality of classes to at least a portion of the expression signals to produce a first preliminary call, the first preliminary call identifying the patient sample as belonging to one or more first classes of the plurality of classes;

applying, by the computer system, a second classification model for the classification scheme to the at least a portion of the expression signals to produce a second preliminary call, the second preliminary call identifying the patient sample as belonging to one or more second classes of the plurality of classes;

combining, by the computer system the first and second preliminary calls to produce a combined call and a weight, the combined call identifying the patient sample as belonging to one class of the plurality of classes, the weight corresponding to the one class; and determining, by the computer system:
whether the weight exceeds a threshold value, and if not, returning an Indeterminable Call, and if so:
comparing the combined call with a verifier to determine consistency, and
if the combined call is not consistent with the verifier, returning an Indeterminable Call, and
if the combined call is consistent with the verifier, returning the combined call.

2. The method of claim 1, wherein each of the first and second classification models includes a set of linear classifiers for class pairs.

3. The method of claim 1, wherein the verifier includes output of a classification model that includes a set of linear classifiers for all classes.

4. The method of claim 1, wherein the classification schema is a 19 class schema, the method further comprising:
comparing the combined call with a second verifier to determine consistency.

5. The method of claim 1, further comprising:
comparing the combined call with a second verifier to determine consistency.

6. The method of claim 1, wherein the first classification model is a pair-wise model, wherein the first classification model provides a first number for each of the one or more first classes, and wherein the combined call is based on the first numbers.

7. The method of 6, wherein:
the second classification model is a pair-wise model;
the second classification model provides a second number for each of the one or more second classes; and
combining the first and second preliminary calls includes:
summing a first number and a second number corresponding to a same class; and
identifying a class having a highest sum.

8. The method of claim 7, wherein summing the first number and second number corresponds to a third classification model for the classification scheme, and wherein combining the first and second preliminary calls further includes:
using secondary votes of the one or more first classes, of the one or more second classes, and of the class having the highest sum to obtain the combined call and the weight.

9. The method of claim 1, wherein combining the first and second preliminary calls to produce the combined call includes:
determining a secondary vote for each of the one or more first classes and for each of the one or more secondary classes, a secondary vote for one of the first classes depending on how many first classes exist, and a secondary vote for one of the second classes depending on how many second classes exist; and
using the secondary votes to determine the combined call and the weight.

10. The method of claim 9, wherein the weight corresponds to a percentage of the secondary votes received by the one class of the combined call.

11. The computer readable medium of claim 9, wherein the weight corresponds to a percentage of the secondary votes received by the one class of the combined call.

12. A non-transitory computer readable medium that stores code, which when executed by one or more processors automatically classify microarray data of a patient sample, the code including instructions to:
automatically generate a plurality of expression signals based on microarray data representing a plurality of probes on a microarray;
a first classification model for a classification scheme having a plurality of classes to at least a portion of the expression signals to produce a first preliminary call, the first preliminary call identifying the patient sample as belonging to one or more first classes of the plurality of classes;
apply a second classification model for the classification scheme to the at least a portion of the expression signals to produce a second preliminary call, the second preliminary call identifying the patient sample as belonging to one or more second classes of the plurality of classes;
combine the first and second preliminary calls to produce a combined call and a weight, the combined call identifying the patient sample as belonging to one class of the plurality of classes, the weight corresponding to the one class; and
determine whether the weight exceeds a threshold value, and if not, returning an Indeterminable Call, and if so:
comparing the combined call with a verifier to determine consistency, and
if the combined call is not consistent with the verifier, returning an Indeterminable Call, and
if the combined call is consistent with the verifier, returning the combined call.

13. The computer readable medium of claim 12, wherein each of the first and second classification models includes a set of linear classifiers for class pairs.

14. The computer readable medium of claim 12, wherein the verifier includes output of a classification model that includes a set of linear classifiers for all classes.

15. The computer readable medium of claim 12, wherein the classification schema is a 19 class schema.

16. The computer readable medium of claim 15, wherein the code further includes instructions to:
compare the combined call with a second verifier to determine consistency.

17. The computer readable medium of claim 12, wherein the code further includes instructions to:
compare the combined call with a second verifier to determine consistency.

18. The computer readable medium of claim 12, wherein:
the first classification model is a pair-wise model
the second classification model is a pair-wise model;
the first classification model provides a first number for each of the one or more first classes;
the second classification model provides a second number for each of the one or more second classes; and
combining the first and second preliminary calls includes:
summing a first number and a second number corresponding to a same class; and
identifying a class having a highest sum.

19. The computer readable medium of claim 18, wherein summing the first number and second number corresponds to a third classification model for the classification scheme, and wherein combining the first and second preliminary calls further includes:
using secondary votes of the one or more first classes, of the one or more second classes, and of the class having the highest sum to obtain the combined call and the weight.

20. The computer readable medium of claim 12, wherein combining the first and second preliminary calls to produce the combined call includes:

determining a secondary vote for each of the one or more first classes and for each of the one or more secondary classes, a secondary vote for one of the first classes depending on how many first classes exist, and a secondary vote for one of the second classes depending on how many second classes exist; and using the secondary votes to determine the combined call and the weight.

\* \* \* \* \*